United States Patent [19]

Singh et al.

[11] Patent Number: 5,945,398
[45] Date of Patent: Aug. 31, 1999

[54] PHARMACEUTICAL COMPOSITIONS CONTAINING CYCLOSPORIN

[75] Inventors: Amarjit Singh; Rajesh Jain, both of New Delhi, India

[73] Assignee: Panacea Biotec Limited, New Delhi, India

[21] Appl. No.: 09/094,267

[22] Filed: Jun. 9, 1998

[51] Int. Cl.$^6$ .......................... A61K 38/00; A61K 38/12; C07K 5/00; C07K 7/00
[52] U.S. Cl. ................................. 514/11; 514/9; 530/317
[58] Field of Search ................................. 530/317; 514/9, 514/11

[56] References Cited

U.S. PATENT DOCUMENTS

| | | | |
|---|---|---|---|
| 3,288,824 | 11/1966 | Mahler et al. | 260/410.6 |
| 4,108,985 | 8/1978 | Ruegger et al. | 424/177 |
| 4,210,581 | 7/1980 | Ruegger et al. | 260/112.5 R |
| 4,220,641 | 9/1980 | Traber et al. | 424/177 |
| 4,388,307 | 6/1983 | Cavanak | 424/177 |
| 4,719,239 | 1/1988 | Muller et al. | 514/785 |
| 4,835,002 | 5/1989 | Wolf, et al. | 426/590 |
| 4,914,188 | 4/1990 | Dumont et al. | 530/317 |
| 4,990,337 | 2/1991 | Kurihara et al. | 424/427 |
| 4,996,193 | 2/1991 | Hewitt et al. | 514/11 |
| 5,342,625 | 8/1994 | Hauer et al. | 424/455 |
| 5,639,724 | 6/1997 | Cavanak | 514/11 |

FOREIGN PATENT DOCUMENTS

| | | |
|---|---|---|
| 895724 | 7/1983 | Belgium . |
| 2098865 | 12/1982 | United Kingdom . |
| 9613273 | 5/1996 | WIPO . |

OTHER PUBLICATIONS

Chemical Abstracts, vol. 89, No. 89: 117875t (1978).
Chemical Abstracts, No. 92: 64765k (1980).
Chemical Abstracts, vol. 94, No. 94: 327c (1981).
Chemical Abstracts, vol. 95, No. 95: 225610k (1981).
Sokol, R. J., et al. "Improvement of cyclosporin absorption in children after liver transplantation by means of water–soluble vitamin E." The Lancet, vol. 338 (July 1991) pp. 212–215.
Bulletin Technique Gattefosse, No. 87 (1994), p. 72.
Bulletin Technique Gattefosse, No. 87 (1994).
Microemulsions: Formulation Guide, Gattefosse, p. 6.
Takada, K., et al., International Journal of Pharmaceutics, vol. 44 (1988) pp. 107–116.

*Primary Examiner*—Avis M. Davenport
*Attorney, Agent, or Firm*—Ladas & Parry

[57] ABSTRACT

A novel homogenous alcohol free, free flowing, clear and transparent pharmaceutical composition containing Cyclosporin is disclosed. The amount of Cyclosporin is easily measurable at a wide range of temperature of 15° to 45° C. The composition comprises a Cyclosporin in a hydrophillic carrier medium comprising propylene glycol, a transesterification product of a natural vegetable oil triglyceride and a polyalkylene polyol and polyethylene hydrogenated castor oils.

9 Claims, No Drawings

PHARMACEUTICAL COMPOSITIONS CONTAINING CYCLOSPORIN

INTRODUCTION

The present invention relates to a novel homogenous alcohol free, free flowing, clear and transparent pharmaceutical composition comprising a Cyclosporin as active ingredient. The novel composition is characterised in having increased bio-availability when the drug is formulated in a solubilised system and also amenable to convenient commercial production.

BACKGROUND OF THE INVENTION

Cyclosporins comprise a class of structurally distinctive, cyclic, poly-N-methylated endecapeptides, commonly possessing pharmacological, in particular immunosuppressive, anti-inflammatory and/or anti-parasitic activity. The first of the Cyclosporins to be isolated was the naturally occurring fungal metabolite Ciclosporin or Cyclosporine, also known as Cyclosporin A and commercially available under several brands. Ciclosporin is the Cyclosporin of formula A.

proposed or applied include, autoimmune hematological disorder (including e.g. hemolytic anaemia, aplastic anaemia, pure red cell anaemia and idiopathic thrombocytopaenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine opthalmopathy, Graves disease, sarcoidosis, multiple sclerosis, primary biliary cirrhosis, juvenile diabetes (diabetes mellitus type 1), uveitis (anterior and posterior), keratoconjunctivitis sicca and vernal keratoconjunctivitis, interstitial lung fibrosis, psoriatic arthirits and glomerulonephritis (with and without nephrotic syndrome, e.g. including idiopathic nephrotic syndrome or minimal change nephropathy).

Further areas of investigation have been potential applicability as an anti-parasitic, in particular anti-protozoal agent, with possible uses suggested including treatment of malaria, coccidiomycosis and schistosomiasis and, yet more recently, use as an agent for reversing or abrogating anti-neoplastic agent resistance in tumours and the like.

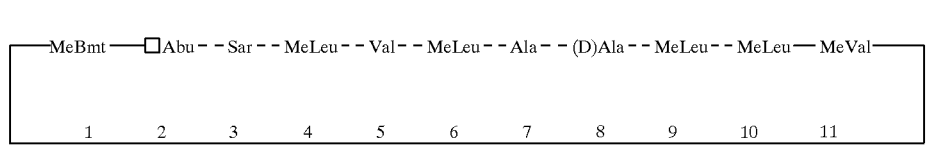

(A)

wherein—MeBmt—represents the N-Methyl-(4R)-4-but-2E-en-1-yl-4-methyl-(L)threonyl residue of formula B.

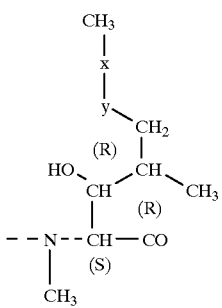

(B)

in which —x—y— is —CH=CH— (trans).

So far the primary area of clinical investigation for Ciclosporin has been as an immunosuppressive agent, in particular in relation to its application to recipients of organ transplants, e.g. heart, lung, combined heart-lung, liver, kidney, pancreatic, bone-marrow, skin and corneal transplants and, in particular, allogenic organ transplants. In this field Ciclosporin has achieved a remarkable success in its usage.

At the same time, applicability of Ciclosporin to various autoimmune diseases and to inflammatory conditions, in particular inflammatory conditions with an aetiology including an autoimmune component such as arthritis (for example rheumatoid arthritis, arthritis chronica progrediente and arthritis deformans) and rheumatic diseases, has been intensive and reports and results in vitro, in animal models and in clinical trials are widespread in the literature. Specific autoimmune diseases for which Ciclosporin therapy has been A detailed write-up on the variety of naturally occurring and semi-synthetic Cyclosporins, their classification, nomendature etc. has already been published [c.f Traber et al. 1, Helv. Chim Acta. 60, 1247–1255 (1977); Traber et al. 2, Helv. Chim. Acta. (65 no. 162, 1655– 1667 (1982); Kobel et al., Europ. J. Applied Microbiology and Biotechnology 14, 273–240 (1982); and von Wart-burg et al., Progress in Allergy, 38, 28–45 (1986)]. U.S. Pat. Nos. 4,108,985, 4,210, 581 and 4,220,641; European Patent Publication Nos. 0 034 567 and 0 056 782; International Patent Publication No. WO 86/02080; Wenger 1, Transp. Proc. 15, Suppl. 1;2230 (1983); Wenger 2, Angew. Chem. Int. Ed.,24, 77 (1985); and Wenger 3, Progress in Chemistry of Organic Natural Products 50, 123 (1986). Among all the Cyclosporins, Cyclosporin A (also known as Ciclosporin or Cyclosporine) has established its utility in the area of organ transplant and therapy of autoimmune diseases.

Although Cyclosporin is used most widely amongst all the immunosuppresants available so far, it suffers from a serious drawback of poor bio-availability.

The oral dosage forms existing lately in the market (i.e. those employing ethanol, olive oil as carrier medium in conjunction with Labrafill as surfactant (U.S. Pat. No. 4,388,307) are unpleasant tasting galenic forms. The bio-availability levels using these dosage forms are low and exhibit wide inter-and intra-individual variations. Such dosage forms provide an average absolute bioavailability of ca 30%. Reported variation in bio-availability between subjects varies between a few percent for some patients to as much as 90% or more for others. Also a marked change in bio-availability for individuals with time is frequently observed.

Cyclosporin blood levels have to be maintained within a specified range to achieve the effective therapy. The required range varies according to the clinical status of the patient.

Because of poor and variable bioavailability daily dosages need to achieve the desired blood levels need to be varied considerably in the existing dosage forms of Cyclosporin and a concomitant monitoring of blood levels is essential. This adds an additional cost to be therapy.

In order to improve the bio-availibility several attempts have been made to improve formulations of Cyclosporin.

U.S. Pat. No. 4,388,307 has proposed a method of preparation of drinks solution containing Cyclosporin in a base of Labrafil, Miglyol, Ethanol, Corn/olive oil. However, such preparation suffered from the draw back that it can be presented only as a liquid for dilution in drinking water/fluid before use, otherwise it is very difficult to give an accurate dose. Bioavailability levels achieved using the systems is very low and exhibits wide variations between individuals, individual patient type and even for single individuals at different times using the course of therapy.

Han Gua Patent (Reference from Chinese Patent no. 94191895.5) explains the active compound of Cyclosporin, fatty acid sugar ester and diluent carrier having good bioavailability. However, this compound suffers from the drawback that diluent degrades due to hygroscopicity of sugar ester and the stability is not of desired standards, (See also Pharmaceutical Research, Volume 6, No. 11, 1989, P958, "Solid Surfactant Solution of active Ingredients in Sugar Ester" and International Journal of Pharmaceutics, Vol. 92, 1993, P197, "Application of sucrose laurate a new pharmaceutical excipient, in Peroral formulation of Cyclosporin A").

Chinese patent 9419189.5 having equivalent EP 0702562 describes a powder dosage form of Cyclosporin possessing comparatively higher stability and to some extent bioavailability when compared to the earlier formulations. This Patent claims a bioavailability of the Composition as 62% higher than that of the composition of U.S. Pat. No. 4,388,307 of Sandoz. This art describes absorption of Cyclosporin A with appropriate solvents on to a adsorbent along with a nonionic hydrophillic surfactant. The final product does not contain the solvent as this evaporates during the process of manufacturing. Thus this product does not suffer from the disadvantage arising out of solvent evaporation during shelf life and hence stability problems. The various pharmaceutical surfactants, polyhydric alcohols and solvents are well known to the art. The adsorbent used is Colloidal Silicon Dioxide. The blood level arising out of such product have been compared with the standard formulations as per U.S. Pat. No. 4,388,307 with significant improvement in bioavailability. However, if compared with the micro-emulsion based formulations these formulations do not show any advantage as the drug is adsorbed on solid surface and needs an additional process of dissolution prior to become bioavailable.

The effect of sucrose laurate on the gastrointestinal absorption of Cyclosporin is also described (Lerk-PC; Sucker-H, International-Journal-of-Pharmaceutics; 1993; 92; (May 3); 197–202). The evaluation of the dosage form containing sucrose Laurate was found to enhance the in vitro absorption of Cyclosporin when normal epithelial tissue and Peyer's patch tissue of guinea pigs were used. Compared to the commercially available drinking solution, absorption was raised by a factor of 10. Excess amount of surfactant reduced drug absorption. Despite large excess of Sucrose laurate, the absorption of Cyclosporin was still superior to the drinking solution. Choleic acid was also found to increase absorption by a factor of 5–6. A comparison of the absorption between normal epithelial and Peyer's patch tissues indicated that the absorption by endocytosis does not contribute significantly to the overall absorption of Cyclosporin. It was concluded that preliminary formulation experiments showed that a solid oral dosage form of Cyclosporin could be made using sucrose laurate as an excipient.

Several formulations of Cyclosporin were prepared and examined in vitro and in dogs Abdallah-HY, Mayersohn-M. Pharmaceutical Research; 1991;8(April),518–522. A tablet formulation was then selected for comparison with the commercial oil solution placed in a soft gelatin capsule in a randomized crossover study in dogs. Compared with an intravenous dose of the drug, absolute bioavailability was 46+11.1 and 45+9.9% for the capsules and tablets, respectively. Maximum concentration, time to reach maximum concentration and mean absorption time were not significantly different between the 2 formulations. It was concluded that the tablet formulation of Cyclosporin is equivalent in dogs to the commercial dosage form placed into soft gelatin capsules.

U.S. Pat. No. 5,051,402 describes that Cyclosporin may be renderred more soluble by the concomitant administration of α-Cyclodextrin, either separately, but essentially simultaneously or, preferably, in admixture.

U.S. Pat. No. 4,990,337 describes a formulation of alongwith mixture of Cyclosporin of mono or diglyceride fatty acids. They may be rendered more soluble or dispersible in aqueous media by first dissolving them in at least one mono-or diglyceride of a $C_6$–$C_{10}$ fatty acids, and the resulting solution can then easily be emulsified in water or an aqueous fluid. It is persumed that the more soluble preparations may have increased bio-availability.

Freeze dried liposome mixture containing Cyclosporin has been described in U.S. Pat. No. 4,963,362. This invention provides a freeze-dried potential liposome mixture having an amphipathic lipid and a Cyclosporin or derivative thereof for use in possible liposime delivery of Cyclosporin into cells. A method to produce the freeze-dried mixture is also disclosed. When reconstituted to yield liposomes in an aqueous medium, substantially all of the Cyclosporin present in the freeze-dried mixture is encapsulated in the liposomes.

Other galenic improvements in Cyclosporin emulsion formulations are recorded in prior art are the use of tocopherol derivatives (EP 0724452), tocophereyl polyethyleme glycol carboxylic acid ester (EP 0712631), dimethylisosorbide (EP 0711550, EP 0650721), alkylene polyether or polyester (WO 9423733), emulsion compositions (EP 0694308), anhydromannitol oleylether, lactoglyceride, citroglycerides (EP 656212), phosphatidyl ethanolamine (EP 0651995), as surfactants and stabilizers etc.

Three Patent Applications namely European Patent App. No. 94110184.2, 95117171.9 and PCT/EP95/04187 describe the use of Dimethyl Isosorbide. While European Patent App. No. 94110184.2 and 95117171.9 use dimethyl isosorbide as a co-surfactant, PCT/EP95/04187 describe the use of dimethyl isosorbide or a hydrophillic phase component.

One of the most significant attempt to improve bioavailability of Cyclosporin from its dosage form is the described in U.S. Pat. No. 5,342,625. This art describes use of microemulsion pre-concentrate consisting of a three phase systems i.e. (1) a hydrophilic phase component (2) a lipophilic phase component and (3) a surfactant. Such composition has alcohol as an essential ingredient, such composition upon dilution with water provides an oil-in-water microemulsion with an average particle size of less than 1000 Å. Such an enhanced surface area results in increased bio-availability of Cyclosporin when compared with conventional dosage forms. A comparison of bio-availability form micro-emulsion dosage form (Composition I from U.S. Pat. No. 5,342,625) with the conventional ethanol-oil based dosage form (composition from U.S. Pat. No. 5,342,625), earlier reported in U.S. Pat. No. 4,388,307) has been performed in healthy human volunteers and reported in U.S. Pat. No. 5,342,625. Bio-availability level of 149.0% (±48) is recorded for composition I as compared to composition X (for which bio-availability achieved is set as 100%). The mean AUC levels from composition I were 40% higher when compared to those from composition X but still had a high variation of 20%.

Alcohol is an essential part of composition as is evident from the products available in the market (Sandimun [U.S. Pat. No. 4,388,307] and Neoral [U.S. Pat. No. 5,342, 625]) both of which contain Alcohol. Such composition suffer from severe drawback of instability due to evaporation of a low boiling solvent like Alcohol. This is particularly true as the products are used in home environment, which cannot be precisely controlled with respect to temperature. Although very expensive cumbersome technology (such as cold formed Aluminium/Aluminium Blister packs) is adopted to protect these products, yet the problem of instability is not completely solved. The stability problems are evident from strict storage conditions and usage requirements as declared either on the labels or package inserts of commercial products Sandimun, and Neoral drink solutions and capsules. Some of the examples are:

1. There is a requirement of storage of product below 30° C. at the same time refrigeration is prohibited. This means that a patient using this product in a tropical country need to have an air-conditioned home environment. This is not only a limiting factor in use of this product but sometimes in economically backward countries it may not be possible that every person using the product has an air-conditioned storage area. Sometimes factors like prolong electricity failure and mechanical and electrical defects in air-conditioning system can cause instability problems to these products rendering them unstable for use.

2. There is also an a statement in Packing insert of Sandimun and Neoral drink solutions that "Sandimun Neoral solution should be used within 2 months of opening the bottle and be stored between 15° and 30° C., preferably not below 20° C. for prolonged periods, as it contains oily components of natural origin which tend to solidify at low temperatures. A jelly-like formation may occur below 20° C., which is however reversible at temperatures up to 30° C. Minor flakes or a slight sediment may still be observed. These phenomena do not affect the efficacy and safety of the product, and the dosing by means of the pipette remains accurate." indicating instability problems.

U.S. Pat. No. 5,639,724 discloses pharmaceutical compositions comprising Cyclosporin, transesterification product of a natural vegetable oil with glycerol which is exemplified in the specification as MAISIN (transestrification product of corn oil and glycerol) which is an essential feature of the compositions. This composition necessitates that Cyclosporin be mixed with a transesterification product of a natural vegetable oil with glycerol. Such composition is not fit for drink solution because of formation of jelly like lumps, since the transesterification product is a jelly like substance at room temperature. Such composition also preferably uses alcohol. This compositions compares its bio-availability with that of older and inferior compositions based on U.S. Pat. No. 4,388,307 and does not compare bioavailability with a more recent a marketed compositions (NEORAL) as defined in U.S. Pat. No. 5,342,625.

The formulation of emulsion as well as microemulsion present their own technological problems relating to thermodynamic instability. Such problems may be partially solved by presenting the product in a microemulsion pre-concentrate form wherein the microemulsification occurs in vivo only. However, such systems may also present variability problems due to wide variations existing in GI tract of patients.

Any person skilled in the art attempting to make composition without use of alcohol and without careful and extensive experimentation and study of desired chemicals to be added to Cyclosporin will end with compositions which are highly viscous and which tend to solidify at normal room temperature conditions. Such compositions are undesirable not only due to physical unstability but also that they cannot be formulated as liquids whose dose can be measured exactly under normal conditions.

The major consideration here is the accurate measurement of dose in Cyclosporin which is an essential feature because of the narrow therapeutic condition of the drug i.e. below threshold the organ rejection occurs and above a particular level the drug causes severe toxic reactions.

None of the above mentioned inventions teaches the art of dissolving Cyclosporin (which is a hydrophillic water, unsoluble hydrophobic drug) in a hydrophillic medium. This looks improbable and a person skilled in the art cannot conceive beyond an emulsion and/or a microemulsion.

All the earlier approaches to enhance the bioavailability of Cyclosporin were towards making the drug in a emulsified form (U.S. Pat. No. 4,388,307) or substantially increasing the surface area by converting into microemulsion (U.S. Pat. No. 5,342,625).

MASINE is a fatty acid material which gets out not only when combined with Cyclosporin but even when comprising Labrafil along with MAISINE.

In the body of the specification of U.S. Pat. No. 5,639,724 Labrafil has been disclosed as a preferred ingredient to be added to the composition of Cyclosporin and MAISINE for drink solution. However, this patent does not address the problem of formation of flake like substances formed by the presence of MAISINE even though Labrafil has been added to the composition.

Our attempt has been to effect solution of Cyclosporin in a hydrophillic environment using micellar concept of a surfactant and a co-surfactant such that such compositions are substantially devoid of fatty materials and hence also devoid of the defects associated with such fatty materials. Our composition when diluted with water or aqueous medium retains the lipophillic Cyclosporin drug in a solubilized state. Hence making the drug bioavailable in therapeutic concentrations and with reproducibility.

It will be most appropriate to formulate Cyclosporin compositions in a way that the drug gets converted into a solubilized system on dilution in vivo. The compositions of the invention when administered orally in the form of a drink solution or soft gelatin capsules get diluted with the gastrointestinal fluids to form micellar solutions such that the hydrophillic end of the surfactant and co-surfactant are oriented towards the hydrophillic environment of gastrointestinal fluid and the drug molecules are entrapped in the hydrophobic portions of the surfactant micelles. Such micellar solubilized system, when in contact with the mucosa of the gastrointestinal tract, release the drug leading to absorption; thus providing an increased and less variable bioavailability.

Such systems will definitely be more uniform and bioavailable than microemulsions from where the drug has to partition out of Lipophillic phase for absorption.

Moreover, the inventors have done a detailed study of the type of products developed out of the technology based on microemulsion based systems.

The product existing in the commercial market are presented into two types of oral dosage forms.

One type is the oral solution concentrates to be diluted prior to intake as start up therapies. These dosage forms provide more flexibility in dosage adjustments to achieve the optimum therapeutic concentrations as desired by the physicians.

The second type of dosage forms are unit dosage forms for example Capsules generally soft gelatin capsules. These type of dosage forms are used as continuation therapies once the dosage adjustments have been done.

The inventors have by careful experimentation and expenditure of mental faculties been able to invent a composition in which hydrophobic drug like Cyclosporin can be theorectically dissolved in a hydrophillic medium by careful solution of the hydrophillic medium, surfactants and manner of addition such that a hydrophobic drug can get dissolved in a array of surfactant molecules arranged in a manner that their hydrophillic portion are oriented outside i.e. towards the hydrophillic medium resulting in clear stable solutions. Such products when they come in contact with biological fluids result in total solubilization of Cyclosporin at molecular levels thereby increasing the surface area of Cyclosporin and such diluted solutions of Cyclosporin are highly bioavailable. Such compositions do not remain in emulsion or in microemulsion form.

In another embodiment of the invention there is disclosed an improved process for making soft gelatin capsules containing Cyclosporin as active ingredient in a carrier composition comprising propylene glycol, a transesterification product of a natural vegetable oil triglyceride and a polyalkylene polyol and polyoxyethylene hydrogenated castor oils wherein the ingredients are present in the following range:

Cyclosporin: about 10% w/w
Propylene Glycol: 10–40% w/w
A transesterification product of a natural vegetable oil triglyceride and a polyalkylene polyol: 10–30% w/w
Polyoxyethylene hydrogenated castor oils: 30–50% w/w which comprises adding to the said composition substantially 10–25% excess of the base thereby compensating for the loss of weight due to migration of materials with free hydroxy groups into the capsule shell thus preventing precipitation of drug due to loss of solvent and reducing substantially 10–25% of the polyols such as Sorbitol and Glycerol which are used as plastisizers from the capsule shell.

The term "base" or "carrier medium" should be implied to mean everything added to the composition except the drug.

The amount of plasticizers in the capsule shell are reduced by the amount equivalent to the excess carrier medium added in the capsule.

The composition is incorporated into the capsule shell by conventional procedures as described in standard texts. ("The theory and practice of Industrial Pharmacy" by Leon Lachman et al. third edition, LEA AND FEBIGER U.S.A.).

The Soft Gelatin Capsules have a very distinct advantage of ease of carrying and administration as compared with oral solutions. These dosage forms hence contribute to a very large segment of commercial market.

Such dosage forms that is soft gelatin capsules pose unique technology problems when the compositions to be encapsulated are microemulsion pre-concentrate.

The present invention relates to formulation of Cyclosporin in compositions such that the drug is presented in solubilized systems of surfactant micelles appropriately stabilised in specific Hydrophillic phase.

SUMMARY OF THE INVENTION

In accordance with the present invention there is described a homogenous substantially alcohol free, transparent composition of Cyclosporin which is clear, stable, flowable and easily measurable at a wide range of temperature of 15° to 45° C. which comprises a Cyclosporin in a hydrophillic carrier medium comprising propylene glycol, a transesterification product of a natural vegetable oil triglyceride and a polyalkylene polyol and polyoxyethylene hydrogenated castor oils wherein the ingredients are present in the following range:

Cyclosporin: about 10% w/w
Propylene Glycol: 10–40% w/w
A transesterification product of a natural vegetable oil triglyceride and a polyalkylene polyol: 10–30% w/w
Polyoxyethylene hydrogenated castor oils: 30–50% w/w Preferably the transesterification product of a natural vegetable oil triglyceride and a polyalkylene polyol is Apricot Kernel Oil Polyethylene glycol 6 esters. More preferably the Apricot Kernel Oil Polyethylene glycol 6 ester is Labrafil M1944.

Preferably the polyoxyethylene hydrogenated castor oil is Cremophor RH 40.

Preferably the ingredients in the present compositions are present in the following range:

Cyclosporin: about 10% w/w
Propylene Glycol: 15–30% w/w
A transesterification product of a natural vegetable oil triglyceride and a polyalkylene polyol: 15–28% w/w
Polyoxyethylene hydrogenated castor oils: 15–45% w/w More preferably the composition in accordance with the present invention comprises the ingredients in the following range:

Cyclosporin: about 10 % w/w
Propylene Glycol: 25% w/w
A transesterification product of a natural vegetable oil triglyceride and a polyalkylene polyol: 25% w/w
Polyoxyethylene hydrogenated castor oils: 40% w/w

DETAILED DESCRIPTION OF THE INVENTION

The systems of the present invention are single phase systems in contrast to emulsion/microemulsions wherein essentially Lipophillic phase is emulsified or microemulsified with Hydrophillic phase using surfactant.

The expression "single phase" should be implied to mean a phase wherein the drug is solubilised in Hydrophillic phase using suitable surfactant(s)/co-surfactant(s).

The compositions in this invention are substantially free of ethanol.

It is most beneficial in context of hot tropical countries where absence of $C_{1-5}$ alkanols such as ethanols are more due to evaporation.

Such compositions of the present invention which are solubilized systems and substantially free of $C_{1-5}$ alkanols such as ethanol are distinctly advantageous over the ones described in U.S. Pat. No. 5,342,625 with respect to manufacturing and distribution in the tropical countries.

In accordance with the present invention there is described a homogenous substantially alcohol free, transparent composition of Cyclosporin which is clear, stable, flowable and easily measurable at a wide range of temperature of 15° to 45° C. which comprises a Cyclosporin in a hydrophillic carrier medium comprising propylene glycol, a transesterification product of a natural vegetable oil triglyceride and a polyalkylene polyol and polyoxyethylene hydrogenated castor oils wherein the ingredients are present in the following range:

Cyclosporin: about 10% w/w

Propylene Glycol: 10–40% w/w

A transesterification product of a natural vegetable oil triglyceride and a polyalkylene polyol: 10–30% w/w Polyoxyethylene hydrogenated castor oils: 30–50% w/w Preferably the transesterification product of a natural vegetable oil triglyceride and a polyalkylene polyol is Apricot Kernel Oil Polyethylene glycol 6 esters. More preferably the Apricot Kernel Oil Polyethylene glycol 6 ester is Labrafil M1944.

Preferably the polyoxyethylene hydrogenated castor oil is Cremophor RH 40.

Preferably the ingredients in the present compositions are present in the following range:

Cyclosporin: about 10% w/w

Propylene Glycol: 15–30% w/w

A transesterification product of a natural vegetable oil triglyceride and a polyalkylene polyol: 15–28% w/w Polyoxyethylene hydrogenated castor oils: 15–45% w/w More preferably the composition in accordance with the present invention comprises the ingredients in the following range:

Cyclosporin: about 10% w/w

Propylene Glycol: 25% w/w

A transesterification product of a natural vegetable oil triglyceride and a polyalkylene polyol: 25% w/w Polyoxyethylene hydrogenated castor oils: 40% w/w Very small amounts of Antioxidants usually in the range 0.005% to 0.01% w/w may be present as a part of one of one of the ingredients of the composition.

The amounts of the ingredients to the composition disclosed above equals to 100%.

The formulation can be prepared so as to be diluted as a drink solution or incorporated into soft gelatin capsules.

The term "easily measurable" has been used due to the characteristic features of the drug Cyclosporin. Cyclosporin requires accurate dose measurement because of its narrow therapeutic index. Most of the drink solution packs are provided with a pipette or a syringe for accurate dose measurement. This warrants that the solution is a sufficiently thin liquid to permit ease of measurement and not a semi-solid mass and also it should be devoid of any flakes, jelly like formations or other sediments which can cause non-homogenity in the dose. The composition of our invention possesses all the desired characteristics and hence is easily measurable as far as the dose requirement is concerned.

In accordance with another embodiment of the invention a composition is disclosed which is a homogenous substantially alcohol free, transparent composition of Cyclosporin which is clear, stable, flowable and easily measurable at a wide range of temperature of 15° to 45° C. which comprises a Cyclosporin in a hydrophillic carrier medium comprising Triacetin, Propylene Glycol and Polyoxyethylene hydrogenated castor oils wherein the ingredients are present in the following range:

Cyclosporin: about 10% w/w

Propylene Glycol: 10–40% w/w

Triacetin: 10–30% w/w

Polyoxyethylene hydrogenated castor oils: 30–50% w/w

Very small amounts of Antioxidants usually in the range 0.005% to 0.01% w/w may be present as a part of one of one of the ingredients of the composition.

The amounts of the ingredients to the composition disclosed above equals to 100%.

The formulation can be prepared so as to be diluted as a drink solution or incorporated into soft gelatin capsules. A "drink solution" should be implied to mean a homogenous clear transparent, stable, flowable and easily measurable liquid at a wide range of temperature i.e from 15° C. to 45° C. which can be packed in a suitable container from which requisite amount can be withdrawn with the help of a pipette or syringe.

Preferably the polyoxyethylene hydrogenated castor oil is Cremophor RH 40.

Preferably such composition further comprises Oleic acid. Such Oleic acid may be present in the range from 0–10% w/w.

Several compositions as per this invention with different ranges of ingredients were subjected to commercial production trials and shelf-life stability studies and the inventors were successful in arriving at a composition which was easy to manufacture and stable for long periods of time when tested by accelerated stability studies.

Moreover when tested on healthy human volunteers, the composition(s) of this invention was found to have excellent bio-availability of Cyclosporin and were also found to be bioequivalent with commercial products. The comparitive results are collected in Table I & II.

The invention will now be described with reference to the accompanying examples which should not be construed to limit the scope of the invention:

EXAMPLE 1 (PRIOR ART)

| | COMPONENT | AMOUNT |
|---|---|---|
| a) | Cyclosporin | 100 mg (= ca. 10.5%) |
| b) | Maisine | 550 mg (= ca. 57.8%) |
| c) | Labrafil M 2125 | 300 mg (= ca. 33.5%) |
| | TOTAL | 950 mg |

The mixture obtained was a semi-solid mass at room temperature suitable only for soft gelatin capsule formulation.

EXAMPLE 2 (PRIOR ART)

| | COMPONENT | AMOUNT |
|---|---|---|
| a) | Cyclosporin | 100 mg (= ca. 10.5%) |
| b) | Maisine | 490 mg (= ca. 52%) |
| c) | Labrafil M 2125 | 300 mg (= ca. 31.5%) |
| d) | Cremophore RH40 | 60 mg (= ca. 6.3%) |
| | TOTAL | 950 mg |

The mixture obtained was a semi-solid mass at room temperature suitable only for soft gelatin capsule formulation.

EXAMPLE 3 (PRIOR ART)

|    | COMPONENT  | AMOUNT              |
|----|------------|---------------------|
| a) | Cyclosporin | 100 mg (= ca. 10.5%) |
| b) | Maisine    | 850 mg (= ca. 52%)  |
|    | TOTAL      | 950 mg              |

The mixture obtained was a semi-solid mass at room temperature suitable only for soft gelatin capsule formulation.

EXAMPLE 4 (PRIOR ART)

|    | COMPONENT       | AMOUNT  |
|----|-----------------|---------|
| a) | Cyclosporin     | 100 mg  |
| b) | Propylene Glycol | 200 mg  |
| c) | Cremophore RH40 | 350 mg  |
| d) | Labrafil M1944  | 200 mg  |
| e) | Maisine         | 150 mg  |
|    | TOTAL           | 1000 mg |

The composition obtained was a clear, homogenous liquid at a temperatures between 25° to 30° C., but at temperatures below 20° C. jelly like flakes separated out.
Manufacturing process for compositions 1 to 4

The components are thoroughly admixed in a conventional manner. The mixture so obtained is a semi-solid mass at room temperature suitable only for soft gelatin capsule formulation and not for a drink solution.

EXAMPLE 5

|    | COMPONENT       | AMOUNT  |
|----|-----------------|---------|
| a) | Cyclosporin     | 100 mg  |
| b) | Propylene Glycol | 200 mg  |
| c) | Cremophore RH40 | 415 mg  |
| d) | Labrafil M1944  | 285 mg  |
|    | TOTAL           | 1000 mg |

Above composition gives a clear, homogenous solution which remains clear and stable at temperatures between 15° to 45° C. without any jelly like flake formation. Hence this composition is suitable for formulating as a drink solution or soft gelatin capsules.

EXAMPLE 6

|    | COMPONENT       | AMOUNT  |
|----|-----------------|---------|
| a) | Cyclosporin     | 100 mg  |
| b) | Propylene Glycol | 150 mg  |
| c) | Cremophore RH40 | 500 mg  |
| d) | Labrafil M1944  | 250 mg  |
|    | TOTAL           | 1000 mg |

Above composition gives a clear, homogenous solution which remains clear and stable at temperatures between 15° to 45° C. without any jelly like flake formation. Hence this composition is suitable for formulating as a drink solution or soft gelatin capsules.

EXAMPLE 7

|    | COMPONENT       | AMOUNT  |
|----|-----------------|---------|
| a) | Cyclosporin     | 100 mg  |
| b) | Propylene Glycol | 250 mg  |
| c) | Cremophore RH40 | 350 mg  |
| d) | Labrafil M1944  | 300 mg  |
|    | TOTAL           | 1000 mg |

Above composition gives a clear, homogenous solution which remains clear and stable at temperatures between 15° to 45° C. without any jelly like flake formation. Hence this composition is suitable for formulating as a drink solution or soft gelatin capsules.

EXAMPLE 8

|    | COMPONENT       | AMOUNT  |
|----|-----------------|---------|
| a) | Cyclosporin     | 100 mg  |
| b) | Propylene Glycol | 200 mg  |
| c) | Cremophore RH40 | 425 mg  |
| d) | Triacetin       | 275 mg  |
|    | TOTAL           | 1000 mg |

Above composition gives a clear, homogenous solution which remains clear and stable at temperatures between 15° to 45° C. without any jelly like flake formation. Hence this composition is suitable for formulating as a drink solution or soft gelatin capsules.

EXAMPLE 9

|    | COMPONENT       | AMOUNT  |
|----|-----------------|---------|
| a) | Cyclosporin     | 100 mg  |
| b) | Propylene Glycol | 100 mg  |
| c) | Cremophore RH40 | 415 mg  |
| d) | Labrafil M1944  | 285 mg  |
| e) | Triacetin       | 100 mg  |
|    | TOTAL           | 1000 mg |

Above composition gives a clear, homogenous solution which remains clear and stable at temperatures between 15° to 45° C. without any jelly like flake formation. Hence this composition is suitable for formulating as a drink solution or soft gelatin capsules.

EXAMPLE 10

|    | COMPONENT       | AMOUNT  |
|----|-----------------|---------|
| a) | Cyclosporin     | 100 mg  |
| b) | Propylene Glycol | 250 mg  |
| c) | Cremophore RH40 | 450 mg  |
| d) | Triacetin       | 150 mg  |
| e) | Oleic Acid      | 50 mg   |
|    | TOTAL           | 1000 mg |

The quantity of a) required for a single dose is dissolved in the remaining components using conventional techniques. Heating the mass up to 60° C. may be used to aid dissolution of a).

Above composition gives a clear, homogenous solution which remains clear and stable at temperatures between 15° to 45° C. without any jelly like flake formation. Hence this composition is suitable for formulating as a drink solution or soft gelatin capsules.

Manufacturing process for compositions 5 to 10

Cyclosporin was dissolved in Propylene Glycol with constant stirring. Preferably the mixture was heated upto 60° C. to aid dissolution process. To such mixture were added the remaining ingredients with constant stirring. The resultant solution was filtered through a 2μ glass fibre filter.

EXAMPLE 11

Process for making Soft Gelatin Capsules of Cyclosporin

The compositions as mentioned in the prior art suffer from a disadvantage of migration of carrier medium comprising solvents containing free —OH groups particularly ethanol into the shell leading to precipitation of drug in the capsules. If alcohol is removed it also leads to precipitation of drug.

To overcome this problem we have surprisingly found in the composition of the present invention that by increasing the amount of carrier medium in the core composition by 10–25% at the time of encapsulation and reducing the amount of plasticizers (Sorbitol and Glycerine) in the capsule shell composition by 10–25% yields soft gelatin capsules which on storage attain equilibrium and remain stable throughout the shelf life as exemplified below: Batch size: 1 lac capsules.

Core Composition
- a) Cyclosporin: 5 kg
- b) Carrier Medium*: 55 kg
  *Includes 220% extra carrier medium
  Composition of carrier medium
  i) Propylene Glycol: 12.0 kg
  ii) Cremophore RH40: 24.9 kg
  iii) Labrafil M1944: 18.1 kg Capsule shell composition
- i) Gelatin: 50 kg
- ii) Sorbitol: 8 kg
- iii) Glycerine: 8 kg
- iv) Methyl Paraben: 240 g
- v) Propyl Paraben: 140 g
- vi) Water: 45 kg
- vii) Colour: 400 g

TABLE I

Plasma Concentration Of Cyclosporine (ng/ml) Following Administration Of a Single Oral Dose Of 2.5 mg/kg Body Wt. Cyclosporine
Name of the preparation: Cyclosporine Composition as per Example 5
Cyclosporine Plasma Concentration (ng/ml)

| Time (Hrs.) | 1 | 2 | 3 | 4 | 5 | 6 | 7 | 8 | 9 | 10 | 11 | 12 | Mean | S.D |
|---|---|---|---|---|---|---|---|---|---|---|---|---|---|---|
| Volunteers | | | | | | | | | | | | | | |
| 0 | 0 | 0 | 0 | 0 | 0 | 0 | 0 | 0 | 0 | 0 | 0 | 0 | 0 | 0 |
| 1 | 507.02 | 524.93 | 316.14 | 339.72 | 484.29 | 284.79 | 495.09 | 323.50 | 233.15 | 545.52 | 121.57 | 318.47 | 374.50 | 128.58 |
| 2 | 976.15 | 685.17 | 676.67 | 879.30 | 509.18 | 330.00 | 540.17 | 468.40 | 670.99 | 1050.17 | 496.62 | 572.56 | 654.82 | 207.75 |
| 2 | 767.23 | 720.42 | 752.85 | 834.18 | 493.70 | 358.60 | 496.83 | 440.60 | 741.30 | 864.65 | 751.07 | 513.84 | 644.59 | 163.99 |
| 3 | 583.14 | 529.36 | 582.94 | 984.11 | 651.30 | 388.54 | 622.55 | 314.57 | 652.49 | 615.40 | 468.99 | 438.30 | 569.31 | 162.64 |
| 3 | 440.50 | 532.52 | 338.03 | 957.49 | 950.12 | 493.15 | 610.79 | 241.05 | 439.72 | 579.65 | 340.29 | 418.09 | 528.03 | 215.19 |
| 4 | 344.75 | 310.85 | 209.30 | 425.88 | 390.23 | 152.59 | 456.25 | 170.91 | 342.17 | 340.47 | 252.28 | 110.21 | 292.16 | 107.28 |
| 6 | 166.74 | 183.19 | 110.32 | 376.34 | 213.65 | 56.52 | 244.53 | 125.10 | 113.28 | 112.57 | 194.69 | 59.42 | 163.02 | 85.36 |
| 9 | 108.50 | 118.21 | 86.91 | 112.71 | 84.05 | 38.23 | 81.58 | 64.45 | 73.72 | 89.42 | 112.75 | 41.64 | 84.35 | 25.61 |
| 12 | 106.23 | 119.25 | 32.17 | 75.07 | 67.94 | 29.83 | 45.21 | 38.21 | 29.34 | 50.80 | 46.11 | 33.86 | 56.21 | 28.89 |
| 24 | 42.38 | 7.36 | 4.53 | 10.21 | 3.20 | 0.00 | 0.00 | 13.92 | 0.00 | 0.00 | 0.00 | 0.00 | 6.80 | 11.63 |
| Cmax (ng/ml) | 976.15 | 720.42 | 752.85 | 984.11 | 950.12 | 493.15 | 622.55 | 468.54 | 741.30 | 1050.17 | 751.07 | 572.56 | 654.82 | 215.19 |
| Tmax (hrs.) | 2.00 | 2.50 | 2.50 | 3.00 | 3.00 | 3.50 | 3.00 | 2.00 | 2.50 | 2.00 | 2.50 | 2.00 | 2.54 | 0.48 |
| AUC (0–24) | 3459.60 | 3185.80 | 2543.80 | 4709.40 | 3656.3 | 1717.90 | 3510.30 | 2130.60 | 2769.1 | 3294.90 | 2624.30 | 1886.10 | 3024.80 | 1211.20 |

TABLE II

Plasma Concentration Of Cyclosporine (ng/ml) Following Administration Of A Single Oral Dose Of 2.5 mg/kg Body Wt: Cyclosporine
Name of the preparation: SANDIMUN NEORAL
Mfd. by: SANDOZ
Cyclosporine Plasma Concentration (ng/ml)

| Time (Hrs.) | 1 | 2 | 3 | 4 | 5 | 6 | 7 | 8 | 9 | 10 | 11 | 12 | Mean | S.D |
|---|---|---|---|---|---|---|---|---|---|---|---|---|---|---|
| Volunteers | | | | | | | | | | | | | | |
| 0 | 19.20 | 0.00 | 0.00 | 0.00 | 0.00 | 0.00 | 0.00 | 0.00 | 0.00 | 0.00 | 0.00 | 0.00 | 0.00 | 0.00 |
| 1 | 563.04 | 618.39 | 553.99 | 301.79 | 124.87 | 136.60 | 382.63 | 406.81 | 317.83 | 284.23 | 312.92 | 162.22 | 347.21 | 166.87 |
| 2 | 973.61 | 688.13 | 695.99 | 573.50 | 252.43 | 234.67 | 600.86 | 545.81 | 572.20 | 608.90 | 1005.59 | 609.00 | 613.35 | 230.13 |
| 2 | 799.31 | — | 815.39 | 849.32 | 222.23 | 225.39 | 283.25 | 581.01 | 550.87 | 1113.49 | 975.24 | 629.65 | 586.76 | 344.69 |
| 3 | 871.51 | 648.54 | 564.36 | 654.42 | 292.19 | 147.92 | 292.86 | 395.61 | 389.28 | 958.44 | 1174.33 | 784.34 | 593.24 | 306.57 |
| 3 | 663.07 | 681.19 | 785.13 | 658.20 | 83.34 | 96.44 | 180.02 | 337.68 | 287.32 | 650.95 | — | 476.92 | 403.35 | 274.51 |
| 4 | 479.11 | 508.23 | 203.31 | 220.43 | 126.02 | 155.19 | 167.99 | 258.38 | 131.69 | 374.83 | 413.61 | 390.79 | 301.70 | 242.67 |
| 6 | 244.93 | 219.30 | 150.01 | 315.89 | 54.23 | 100.41 | 155.89 | 155.50 | 73.56 | 209.46 | 196.43 | 236.47 | 176.01 | 76.54 |
| 9 | 173.69 | 239.76 | 138.19 | 187.56 | 45.03 | 30.44 | 213.96 | 61.45 | 46.26 | 135.34 | 114.97 | 98.98 | 119.47 | 64.31 |
| 12 | 89.20 | 185.38 | — | 129.78 | — | 19.41 | 76.61 | 94.40 | — | — | 12.82 | 20.46 | 54.01 | 64.58 |

TABLE II-continued

Plasma Concentration Of Cyclosporine (ng/ml) Following Administration Of A Single Oral Dose Of 2.5 mg/kg Body Wt: Cyclosporine
Name of the preparation: SANDIMUN NEORAL
Mfd. by: SANDOZ
Cyclosporine Plasma Concentration (ng/ml)

| Time (Hrs.) | Volunteers | | | | | | | | | | | | Mean | S.D |
|---|---|---|---|---|---|---|---|---|---|---|---|---|---|---|
| | 1 | 2 | 3 | 4 | 5 | 6 | 7 | 8 | 9 | 10 | 11 | 12 | | |
| 24 | 23.92 | 55.17 | 0.00 | 0.00 | 0.00 | 54.73 | 53.43 | 11.40 | 0.00 | 0.00 | 0.00 | 0.00 | 16.55 | 24.05 |
| Cmax (ng/ml) | 973.61 | 688.13 | 815.39 | 849.32 | 291.19 | 234.67 | 600.86 | 581.01 | 572.2 | 1113.49 | 1174.33 | 784.34 | 723.21 | 278.57 |
| Tmax (hrs.) | 2.50 | 2.00 | 2.00 | 2.00 | 2.50 | 2.00 | 2.00 | 2.00 | 2.00 | 2.00 | 3.00 | 2.50 | 2.20 | 0.40 |
| AUC (0–24) | 4887.00 | 5394.20 | 3136.60 | 4805.00 | 1000.4 | 1527.80 | 2889.20 | 3056.50 | 1730.20 | 3533.40 | 3364.80 | 3118.60 | 3203.6 | 1364.0 |

We claim:

1. A homogenous substantially alcohol free, transparent composition of Cyclosporin which is clear, stable, flowable and easily measurable at a wide range of temperature of 15° to 45° C. which comprises a Cyclosporin in a hydrophillic carrier medium comprising propylene glycol, a transesterification product of a natural vegetable oil triglyceride and a polyalkylene polyol and polyoxyethylene hydrogenated castor oils wherein the ingredients are present in the following range:

Cyclosporin: about 10% w/w

Propylene Glycol: 10–40% w/w

A transesterification product of a natural vegetable oil triglyceride and a polyalkylene polyol: 10–30% w/w Polyoxyethylene hydrogenated castor Oils: 30–50% w/w.

2. A composition as claimed in claim 1 wherein the ingredients are present in the Following range:

Cyclosporin: about 10% w/w

Propylene Glycol: 15–30% w/w

A transesterification product of a natural vegetable oil triglyceride and a polyalkylene polyol: 15–28% w/w Polyoxyethylene hydrogenated castor oils: 15–45% w/w.

3. A composition as claimed in claim 1 wherein the ingredients are present in the following range:

Cyclosporin: about 10% w/w

Propylene Glycol: 25% w/w

A transesterification product of a natural vegetable oil triglyceride and a polyalkylene polyol: 25% w/w Polyoxyethylene hydrogenated castor Oils: 40% w/w.

4. A composition as claimed in claim 1 which on dilution with aqueous media yields solution of Cyclosporin thus favourably affecting absorption.

5. A composition claimed in claim 1 which is used as a Drink Solution.

6. A homogenous substantially alcohol free, transparent composition of Cyclosporin which is clear, stable, flowable and easily measurable at a wide range of temperature of 15° to 45° C. which comprises a Cyclosporin in a hydrophillic carrier medium comprising Triacetin, Propylene Glycol and Polyoxyethylene hydrogenated castor oils wherein the ingredients are present in the following range:

Cyclosporin: about 10% w/w

Propylene Glycol: 10–40% w/w

Triacetin: 10–30% w/w

Polyoxyethylene hydrogenated castor oils: 30–50% w/w.

7. A composition as claimed in claim 6 which further comprises Oleic acid.

8. A composition as claimed in claim 7 wherein Oleic acid is present in the range from 0–10% w/w.

9. A composition as claimed in claim 1 which is formulated into a soft gelatin capsule.

* * * * *

UNITED STATES PATENT AND TRADEMARK OFFICE
CERTIFICATE OF CORRECTION

PATENT NO. : 5,945,398
DATED : August 31, 1999
INVENTOR(S) : Amarjit Singh and Rajesh Jain It is certified that error appears in the above-identified patent and that said Letters Patent are hereby corrected as shown below:

On title page, insert -- [30] Foreign Application Priority Date September 8, 1997

[in] India . . . . 2532/Del/97 --

Signed and Sealed this

Third Day of April, 2001

*Attest:*

NICHOLAS P. GODICI

*Attesting Officer*  *Acting Director of the United States Patent and Trademark Office*